United States Patent [19]

Larsson et al.

[11] Patent Number: 4,708,714
[45] Date of Patent: Nov. 24, 1987

[54] APPARATUS FOR THE SEPARATION OF FRACTIONS FROM BODY FLUIDS

[75] Inventors: Lars-Ake L. Larsson, Loddekopinge; Ake W. Nilsson, Kavlinge; Bo Ingemar W. Johannson; Lars Olof V. Naucler, both of Lund, all of Sweden

[73] Assignee: Gambro Lundia AB, Sweden

[21] Appl. No.: 787,009

[22] Filed: Oct. 11, 1985

Related U.S. Application Data

[63] Continuation of Ser. No. 557,606, Dec. 2, 1983, abandoned.

[30] Foreign Application Priority Data

Dec. 10, 1982 [SE] Sweden ............................ 8207078

[51] Int. Cl.$^4$ ............................................. A61M 1/03
[52] U.S. Cl. ............................................. 604/5; 604/6
[58] Field of Search ............... 128/633, 664, 665, 666; 604/6, 5, 4

[56] References Cited

U.S. PATENT DOCUMENTS

| 3,029,682 | 4/1962 | Wood | 128/633 X |
| 4,043,501 | 8/1977 | Larrabee et al. | 229/14 BE |
| 4,127,111 | 11/1978 | Drolet | 422/44 X |

FOREIGN PATENT DOCUMENTS

| 046470 | 3/1982 | European Pat. Off. | 604/5 |
| 03331 | 10/1982 | World Int. Prop. O. | 604/5 |

OTHER PUBLICATIONS

Nilsson et al., "A Procedure for Removing High Titer Antibodies by Extracorporeal Protein-A-Sepharose Adsorption in Hemophilia: Substitution Therapy and Surgery in a Patient with Hemophilia B and Antibodies", *Blood*, vol. 58, No. 1, Jul. 1981, pp. 38-44.

Primary Examiner—Michael H. Thaler
Attorney, Agent, or Firm—Lerner, David, Littenberg, Krumholz & Mentlik

[57] ABSTRACT

An apparatus is disclosed for the separation of one or more fractions out of whole blood, plasma, or other similar body fluids utilizing an adsorption column comprising means for feeding the fluid to the column and means for the removal of same. The apparatus includes an analyzing device for the coarse analysis of the fluid and a valve device which is adapted to conduct the fluid flow from the column as a function of the analysis carried out to one of two analyzing devices for the fine analysis of the fluid to determine if the fluid is to be conveyed to a collection container, conveyed back to the source or conveyed to a drain.

7 Claims, 4 Drawing Figures

APPARATUS FOR THE SEPARATION OF FRACTIONS FROM BODY FLUIDS

This is a continuation, of application Ser. No. 557,606 filed Dec. 2, 1983, now abandoned.

FIELD OF THE INVENTION

The present invention relates to apparatus for the separation of one or more fractions out of whole blood, plasma, or other similar body fluids. More particularly, the present invention relates to such apparatus that employs adsorption on an adsorption column, and includes means for feeding said fluid to the column and means for the removal of same.

BACKGROUND OF THE INVENTION

Many diseases are due to the immunoprotection of the body having become unbalanced by the formation of undesirable fractions in the blood. For example, in cases of haemophilia, antibodies may be formed against factor VIII or factor IX which normally control the coagulation of the blood.

It is an object of the present invention to remove such undesirable fractions. It is another object to separate the removed fraction for further usage. For example, the antibodies against factor VIII or factor IX in turn may be attached to a column for the separation of just factor VIII or just factor IX from other fluids, such as blood or plasma from blood donors.

If it is desired to remove just the said antibodies against factor VIII or factor IX, a column is used in accordance with the invention comprising just factor VIII or factor IX attached to a carrier. Alternatively, for example, protein A can be bound to the carrier which in turn is capable of binding, among other things, several different types of IgG. It will thus be evident to those of ordinary skill in this art that the invention can be used in conjunction with a number of different adsorption substances.

A known technique for the removal of a fraction in a biological fluid is described in the journal *Blood*, vol. 58, No. 1, July, 1981 by Inga Marie Nilsson, Svante Jonsson, Siv-Britt Sundqvist, Ake Ahlberg and Sven-Erik Bergentz under the title "A Procedure for Removing High-Titre Antibodies by Extracorporeal Protein-A-Sepharose Adsorption in Haemophilia: Substitution Therapy and Surgery in Patients with Haemophilia B and Antibodies." It can be also be applied, however, as mentioned previously, in a more general manner.

In accordance with the aforementioned paper, it is known that, for example, plasma can be separated from whole blood and that, subsequently, factor VIII or factor IX antibodies can be separated from this plasma in one or the other of two columns connected in parallel containing protein A attached to agarose of the type which is sold under the name of Sepharose by Pharmacia Chemicals, Uppsala. When one column has become saturated, the plasma in turn is passed over to the parallel column so as to make possible a regeneration of the first-mentioned column. Prior to this regeneration, the remaining plasma in the column is pressed back to the patient with the help of a flushing liquid. Towards the end of the flushing, the patient is disconnected, and the flushing liquid is passed to a drain. Subsequently, the pH of the column is lowered gradually by means of a further flushing through, this time with the help of a mixture of an acid and a base. When the attached fractions have become detached from the column, this is indicated on a succeeding UV-meter, which in combination with a succeeding pH-meter, conveys the flushing liquid, together with separated fractions, either to a drain or to a collecting receiver just for these fractions.

One disadvantage of this known system, however, is that it requires a UV-meter of such sensitivity that it is unsuitable for disposable usage and can only be reused after sterilization. A further disadvantage thereof is the gradual lowering of the pH of the column, which takes a relatively long time compared to the time required for the detachment of the collected fractions.

SUMMARY OF THE INVENTION

In accordance with the present invention, it has been discovered that these disadvantages can be overcome by means of a very simple analyzing device, which is positioned downstream from the column for the coarse analysis of the fluid coming from the column. The fluid can be made, for example, to pass through a transparent glass pipe or plastic tube, and its turbidity can then be measured with the help of means for analysis which does not come into contact with the fluid, and which consequently, does not have to be sterilized. A possible fine analysis can then take place further downstream, where the fluid is either conducted to the patient, to a drain, or to a collecting receiver for the separated fractions.

More particularly, the present invention relates to an apparatus of the above-mentioned type characterized in that the means for removal of the fluid comprises at least one analyzing device for coarse analysis of the fluid and a valve device which is adapted so as to conduct the fluid flow from the column as a function of the analysis carried out to one of two analyzing devices for the fine analysis of the fluid.

In accordance with one embodiment of the apparatus of the present invention for the separation of a fraction from a biological fluid, utilizing an adsorption column having an adsorption medium thereon, the apparatus includes means for feeding the biological fluid into the adsorption column so as to absorb the fraction into the column and produce a treated biological fluid therein, means for coarse analysis of the treated biological fluid for determining a primary characteristic of the treated biological fluid, primary valve means positioned downstream of the means for coarse analysis, for selectively directing the treated biological fluid to first or second fluid paths based upon the primary characteristic determined by the means for coarse analysis, first means for fine analysis of the treated biological fluid associated with the first fluid path for determining a secondary characteristic of the treated biological fluid, first secondary valve means positioned downstream of the first means for fine analysis for selectively directing the treated biological fluid to third or fourth fluid flow paths, based upon the secondary characteristic determined by the first means for fine analysis, second means for fine analysis of the treated biological fluid associated with the second fluid path, for determining a secondary characteristic of the treated biological fluid, second secondary valve means positioned downstream of the second means for fine analysis, for selectively directing the treated biological fluid to fifth or sixth fluid flow paths, based upon the secondary characteristic determined by the second means for fine analysis.

In accordance with a preferred embodiment of the apparatus for the separation of a fraction from a biological fluid thereof, in addition to such a first adsorption column, the apparatus also includes, a second adsorption column positioned parallel to that first adsorption column, second means for feeding the biological fluid into the second adsorption column so as to absorb the fraction into that column and produce a treated biological fluid therein, second means for coarse analysis of the treated biological fluid for determining a primary characteristic of the treated biological fluid, and second primary valve means positioned downstream of the second means for coarse analysis for selectively directing the treated biological fluid to the first or second fluid paths based upon the primary characteristic determined by the second means for coarse analysis.

In accordance with the embodiment of the apparatus of the present invention, the means for feeding the biological fluid into the adsorption column comprises an entry valve in fluid communication with the biological fluid and a column regenerative fluid, and being capable of alternately feeding the biological fluid and the column regenerative fluid into the column.

In accordance with the preferred embodiment discussed above, in which two columns are employed, the first and second means for feeding the biological fluid into the adsorption columns comprises first and second entry valves, each being in fluid communication with the biological fluid and a column regenerative fluid, wherein the first entry valve is capable of alternately feeding the biological fluid and the column regenerative fluid into the first adsorption column, and the second entry valve is capable of alternately feeding the biological fluid and the column regenerative fluid into the second adsorption column.

In accordance with one embodiment of the apparatus of the present invention, the means for coarse analysis comprises a detector for monitoring a degree of dilution of the treated biological fluid.

In accordance with another embodiment of the apparatus of the present invention, the first means for fine analysis of the treated biological fluid is a pH meter, and preferably the second means for fine analysis of the treated biological fluid is a protein detector for monitoring the fraction to be separated. Preferably, the second means for fine analysis of treated biological fluid is a pH meter and a protein detector positioned serially for monitoring the fraction to be separated.

In accordance with another embodiment of the apparatus of the present invention, the entry valve introduces the column regenerative fluid into the adsorption column to achieve a pH of the column so that there is a rapid lowering of the pH to accelerate the start of regeneration of the column, followed by gradual lowering of the pH during actual regeneration and a rapid increase in pH to terminate the regeneration.

In accordance with a preferred embodiment of the apparatus of the present invention, the third fluid path directs the treated biological fluid to a means for reintroduction of the treated biological fluid into a subject, the fourth and fifth fluid paths direct the treated biological fluid for disposal and the sixth fluid path directs the treated biological fluid to a collection receiver.

Preferably, the analyzing device for coarse analysis is a detector for monitoring the degree of dilution of the treated fluid, e.g. a whole blood detector in the treatment of blood or a plasma detector in the treatment of plasma. Detectors of this type may be of a very simple design, and can consequently be included in the total system as a disposable component.

Columns of the type described above can be very costly and are appropriately constructed, therefore, on a smaller scale. Because of this, the apparatus in accordance with the invention is preferably provided with a valve device arranged upstream of the column which is adapted so that it can alternately convey the treated fluid or a regenerating liquid respectively, and/or a flushing liquid, to the column.

If one desires to collect the separated fraction, it is appropriate to arrange downstream of one of the second analyzing devices a further valve device controlled by the same for conveying the separated fraction to a special collecting receiver.

If the second analyzing device is a combination of a pH meter and a protein detector, it may be adapted to separate for collection all the fluid passed therethrough which contains more than, for example, 20% protein and which has a pH value between, for example, 2 and 6.

Because the columns used, as has been mentioned, may be very expensive, two or more substantially smaller such columns may be arranged in parallel connection for alternate adsorption and regeneration.

By way of example, the columns of this invention can contain factor IX attached to agarose for the removal of antibodies against factor IX or, for example, protein A has been used for the removal of one or more protein fractions of the IgG type. Protein A can also be attached to larger or smaller agarose balls, or larger balls can be used in the treatment of whole blood, whereas the smaller balls can be used for the treatment of pure plasma.

BRIEF DESCRIPTION OF THE DRAWINGS

The invention will be described in further detail with reference to the attached drawings which show the use of a preferred embodiment of the subject of the invention, and which.

DETAILED DESCRIPTION

Figure 1:
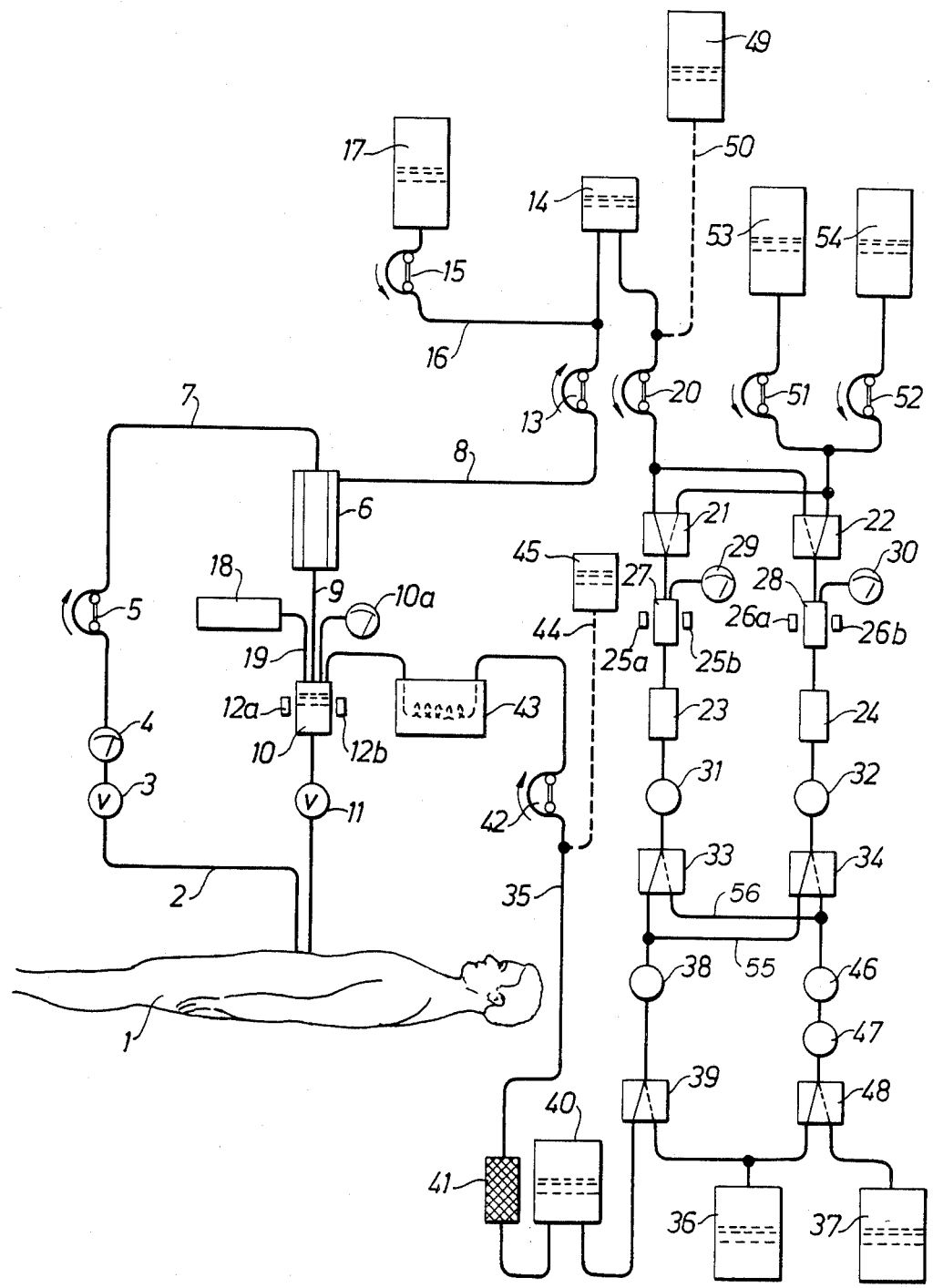
FIG. 1 is a schematic representation of use of the apparatus of the present invention, for particular use in the treatment of plasma.

The present invention will now be discussed in more detail, with reference to the Figures. Referring to FIG. 1, numeral 1 designates the source of the fluid which is to be treated. This source, for example, may be a patient.

From the source 1 the fluid is passed through a line 2, e.g. a plastic tube provided with a cannula via a shut-off clip 3, an arterial pressure gauge 4 and a blood pump 5, to a plasma filter 6. If one is directly treating whole blood rather than plasma, the plasma filter 6 can be eliminated. At a point 7 heparin can be added so as to prevent coagulation of the blood. This herapin addition may also be carried out when the canulla is introduced into the patient.

Through line 8 plasma is withdrawn for further treatment. Red-blood corpuscles and similar molecules or cells which do not pass through the membrane in filter 6 are conducted instead together with a smaller portion of plasma, through a line 9 via a drip chamber 10 and a further shut-off clip 11 back to the patient. Drip chamber 10 is suitably arranged in an air monitor, which may be of the optical or acoustic type. Furthermore, a pressure gauge 10a is connected to the drip chamber 10 for monitoring purposes.

The plasma conveyed through line 8 from the plasma filter 6 is pumped, with the help of a plasma pump 13, up to a plasma reservoir 14. With the help of a second pump 15, a citrate solution from a reservoir 17 for such a solution is conducted by a second pump 15 to the same reservoir, through line 16. This solution is also intended to prevent coagulation. Before any plasma is returned to the patient, this citrate solution is neutralized with the help of a calcium solution from a source 18, which is connected to the drip chamber 10 through line 19.

Plasma from the plasma reservoir 14 is pumped via a plasma pump 20, through one or the other of two valves, 21 and 22, respectively. While it is being treated in one of the two columns, 23 and 24, the second of these columns is appropriately being regenerated at the same time, as will be described below in more detail.

Between valves 21 and 22 and columns 23 and 24, two air monitors are arranged for the protection of columns 23 and 24. These air monitors have been given the designations 25a, 25b, and 26a, 26b, respectively. The air monitors enclose transparent drip chambers, 27 and 28, respectively. Also connected to these drip chambers are pressure guages, 29 and 30, respectively.

From columns 23 and 24, the treated fluid is passed to a means of coarse analysis, such as simple protein detectors, 31 and 32, respectively, to determine a primary characteristic of the fluid. The protein detectors 31 and 32 may be adapted so they directly transilluminate the line being used, if it is made of a transparent material, e.g. plastics. Alternatively, a simple glass tube may be inserted into the line, so as to facilitate such transillumination. The precision required is not great, so the material used can be sufficiently inexpensive for the tube or the line to be discarded after use.

The protein detectors 31 and 32 are followed by two further valves, 33 and 34, respectively. With the help of these valves, and the primary characteristic determined by protein detectors 31 and 32, the treated fluid can be directed to a first or second fluid pathway, 55 and 56 respectively, for eventual return to the patient via a line 35 or to a drain 36 or to a collecting receiver 37 for a required separated fraction.

The division may take place, for example, in such a manner that the protein detectors 31 and 32 perceive when the treated fluid contains more than a certain percentage of protein, e.g. about 70%. If this is the case, the fluid can be conveyed through valves 33 and 34 through the first fluid pathway 55, to a pH meter 38. If the pH measured is too low, e.g. below 6, the fluid is passed via valve 39 to the drain 36. If, on the other hand, the pH is suitable, the fluid can be taken via a reservoir 40, a particle filter 41, a pump 42, and a heating device 43 to drip chamber 10. This thus occurs through line 35. To line 35 may also be conducted a desired diluting and/or replacement liquid via a line 44, from a source 45 for such a liquid. This liquid may, for example, be substantially a sodium chloride solution. However, should it be found, with the help of the protein detectors 31 or 32, that the treated fluid contains less than the required percentage of protein, the fluid can be conveyed through valves 33 and 34, through the second fluid pathway 56, to a pH meter 46 and a more sensitive protein contents meter 47, to a valve 48. If it is thus found with the help of these meters that the protein content and the pH are within certain specified limits, the treated fluid can be directly conducted to the collecting receiver 37 for the separated fraction. If, on the other hand, the pH and protein content measured are outside the specified limits, the fluid can instead be passed, with the help of valve 48, to the drain 36.

To allow the columns 23 and 24 to be flushed clean, it is possible, with the help of the plasma pump 20, to feed a flushing liquid from a source 49 for such a liquid via a line 50.

While one of the columns 23 and 24 is used for adsorption, the other one is appropriately regenerated with the help of an appropriate mixture of a base and an acid which, with the help of pumps 51 and 52, are pumped from sources 53 and 54, respectively, for such materials.

EXAMPLE

Figure 2:
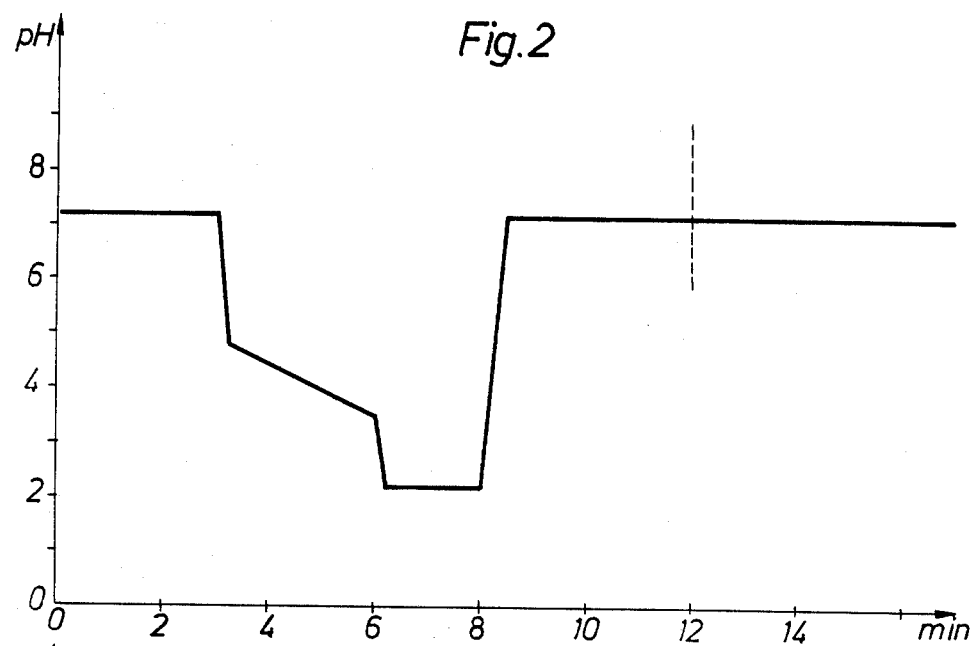
FIG. 2 is a graphical representation showing how the pH of the fluid is appropriately controlled at the input side of the column.
Figure 3:
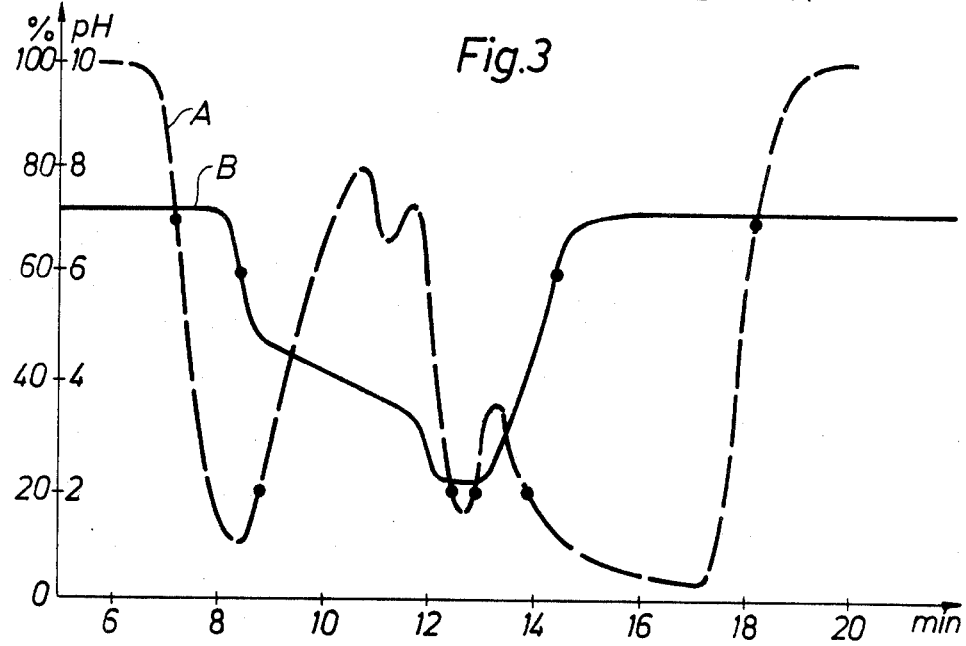
FIG. 3 is a graphical representation showing how the pH and protein content of the fluid vary at the output end of the column, with a shift in time in relation to that of FIG. 2.
Figure 4:
FIG. 4 is a representation showing during which periods set forth in FIGS. 2 and 3 plasma can be returned to the patient, or the treated fluid is conducted to a drain, or to a collecting receiver for the required separated fraction.

In the diagrams shown in FIGS. 2, 3, and 4, a typical regenerating profile is shown by way of example for pH and protein values obtained through the use of the present invention. In the procedure of the example, two columns are used containing 50 ml of gel consisting of protein A attached to agarose of the type which is sold under the name Sepharose CL4 B, by Pharmacia Chemicals, Uppsala. The IgG concentration in the plasma was some 10 mg/ml. The flow of the eluent was approximately 15 ml/min.

In FIG. 2 there is shown the pH value variations at the input side of columns 23 and 24. At time 0 the flushing of a saturated column was commenced. This flushing took place according to the example at a pH value of 7.2. After approximately three minutes of flushing, the pH value dropped rapidly down to approximately 4.8, which is the approximate value at which the attached fraction commences to detach itself. In order to treat the column, as well as the separated fraction, with suitable care, the pH value is controlled slowly down to 3.5. Thereafter, its value is lowered rapidly to approximately 2.2. At this value, the final residues of the attached fraction are separated. After the separation, the column is flushed, restoring the pH value to 7.2. After this, the column is ready for new adsorption.

In FIG. 3 there is shown what occurs at the output side of the column when the pH value is controlled in accordance with FIG. 2. It is noted that there is a time shift on the time axis. The reaction on the output side of the column is thus taking place with a certain delay in relation to the control on the input side of the column. During initial flushing, the protein content diminishes rapidly according to curve A and, as indicated by FIG. 4, the plasma return P to the patient is interrupted at a plasma content of approximately 70%. When the plasma content falls below this value, the treated fluid W commences instead to be conveyed to the drain 36. As the pH value commences to drop in accordance with curve B, further protein A appears in the form of peaks on the curve A. With the help of the valve 48, the fluid F emerging from the regenerated column is then switched over from the drain 36 to the collecting receiver 37, in accordance with what is evident in FIG. 4. Between the peaks of the curve A, the protein content drops below the value of 20%. Such a diluted fraction is not considered to be worth collecting in accordance with the example, and the valve 48 conveys the liquid for a short while to the drain 36. Subsequently, however, a new protein top appears on curve A which is conducted to the collecting receiver 37. The value then drops again to below 20% so that connection to the drain 36 is established and is maintained until the protein content once more rises up to a value of over 70%, that is to say, a while after a new plasma treatment has been started.

Naturally, the invention is not limited exclusively to the example described above with its numerical data or to the preferred embodiment described above, the details of which may be varied in fact within wide limits as is evident from the following claims.

What is claimed is:

1. An apparatus for the separation of a fraction from a biological fluid to provide a treated biological fluid to be supplied to a patient, said apparatus utilizing an adsorption column having an adsorption medium thereon comprising:
   (a) means for feeding said biological fluid into said adsorption column so as to adsorb said fraction into said column and produce a treated biological fluid therein;
   (b) means for coarse analysis of said treated biological fluid for determining a primary characteristic of said treated biological fluid;
   (c) means for supplying said treated biological fluid from said adsorption column to said means for coarse analysis, said means for supplying said treated biological fluid including a removable, disposable portion through which said treated biological fluid flows and arranged within said means for coarse analysis, said disposable portion having walls separating said treated biological fluid from said means for coarse analysis and through which said means for coarse analysis is operative for determining said primary characteristics of said treated biological fluid, whereby said disposable portion can be replaced while retaining said means for coarse analysis;
   (d) primary valve means positioned downstream of said means for coarse analysis for selectively directing said treated biological fluid to first or second fluid paths based upon said primary characteristic determined by said means for coarse analysis;
   (e) first means for fine analysis of said treated biological fluid associated with said first fluid path for determining a secondary characteristic of said treated biological fluid;
   (f) first secondary valve means positioned downstream of said first means for fine analysis for selectively directing said treated biological fluid to third or fourth fluid paths based upon said secondary characteristic determined by said first means for fine analysis, said third fluid path supplying said treated biological fluid to a patient;
   (g) second means for fine analysis of said treated biological fluid in fluid communication with said second fluid path for determining a secondary characteristic of said treated biological fluid; and
   (h) second secondary valve means positioned downstream of said second means for fine analysis for selectively directing said treated biological fluid to fifth or sixth fluid paths based upon said secondary characteristics determined by said second means for fine analysis,
said means for coarse analysis comprising a detector for monitoring a degree of dilution of said treated biological fluid.

2. An apparatus for the separation of a fraction from a biological fluid to provide a treated biological fluid to be supplied to a patient, said apparatus utilizing an adsorption column having an adsorption medium thereon comprising:
   (a) means for feeding said biological fluid into said adsorption column so as to adsorb said fraction into said column and produce a treated biological fluid therein;
   (b) means for coarse analysis of said treated biological fluid for determining a primary characteristic of said treated biological fluid;
   (c) means for supplying said treated biological fluid from said adsorption column to said means for coarse analysis, said means for supplying said treated biological fluid including a removable, disposable portion through which said treated biological fluid flows and arranged within said means for coarse analysis, said disposable portion having walls separating said treated biological fluid from said means for coarse analysis and through which said means for coarse analysis is operative for determining said primary characteristics of said treated biological fluid, whereby said disposable portion can be replaced while retaining said means for coarse analysis;
   (d) primary valve means positioned downstream of said means for coarse analysis for selectively directing said treated biological fluid to first or second fluid paths based upon said primary characteristic determined by said means for coarse analysis;
   (e) first means for fine analysis of said treated biological fluid associated with said first fluid path for determining a secondary characteristic of said treated biological fluid;
   (f) first secondary valve means positioned downstream of said first means for fine analysis for selectively directing said treated biological fluid to third or fourth fluid paths based upon said secondary characteristic determined by said first means for fine analysis, said third fluid path supplying said treated biological fluid to a patient;
   (g) second means for fine analysis of said treated biological fluid in fluid communication with said second fluid path for determining a secondary characteristic of said treated biological fluid; and
   (h) second secondary valve means positioned downstream of said second means for fine analysis for selectively directing said treated biological fluid to fifth or sixth fluid paths based upon said secondary characteristics determined by said second means for fine analysis,
said first means for fine analysis of said treated biological fluid being a pH meter.

3. An apparatus for the separation of a fraction from a biological fluid to provide a treated biological fluid to be supplied to a patient, said apparatus utilizing an adsorption column having an adsorption medium thereon comprising:
   (a) means for feeding said biological fluid into said adsorption column so as to adsorb said fraction into said column and produce a treated biological fluid therein;

(b) means for coarse analysis of said treated biological fluid for determining a primary characteristic of said treated biological fluid;

(c) means for supplying said treated biological fluid from said adsorption column to said means for coarse analysis, said means for supplying said treated biological fluid including a removable disposable portion through which said treated biological fluid flows and arranged within said means for coarse analysis, said disposable portion having walls separating said treated biological fluid from said means for coarse analysis and through which said means for coarse analysis is operative for determining said primary characteristics of said treated biological fluid, whereby said disposable portion can be replaced while retaining said means for coarse analysis;

(d) primary valve means positioned downstream of said means for coarse analysis for selectively directing said treated biological fluid to first or second fluid paths based upon said primary characteristic determined by said means for coarse analysis;

(e) first means for fine analysis of said treated biological fluid associated with said first fluid path for determining a secondary characteristic of said treated biological fluid;

(f) first secondary valve means positioned downstream of said first means for fine analysis for selectively directing said treated biological fluid to third or fourth fluid paths based upon said secondary characteristic determined by said first means for fine analysis, said third fluid path supplying said treated biological fluid to a patient;

(g) second means for fine analysis of said treated biological fluid in fluid communication with said second fluid path for determining a secondary characteristic of said treated biological fluid; and (h) second secondary valve means positioned downstream of said second means for fine analysis for selectively directing said treated biological fluid to fifth or sixth fluid paths based upon said secondary characteristic determined by said second means for fine analysis, said second means for fine analysis of said treated biological fluid being a protein detector for the monitoring of said fraction to be separated.

4. An apparatus for the separation of a fraction from a biological fluid to provide a treated biological fluid to be supplied to a patient, said apparatus utilizing an adsorption column having an adsorption medium thereon comprising:

(a) means for feeding said biological fluid into said adsorption column so as to adsorb said fraction into said column and produce a treated biological fluid therein;

(b) means for coarse analysis of said treated biological fluid for determining a primary characteristic of said treated biological fluid;

(c) means for supplying said treated biological fluid from said adsorption column to said means for coarse analysis, said means for supplying said treated biological fluid including a removable, disposable portion through which said treated biological fluid flows and arranged within said means for coarse analysis, said disposable portion having walls separating said treated biological fluid from said means for coarse analysis and through which said means for coarse analysis is operative for determining said primary characteristics of said treated biological fluid, whereby said disposable portion can be replaced while retaining said means for coarse analysis;

(d) primary valve means positioned downstream of said means for coarse analysis for selectively directing said treated biological fluid to first or second fluid paths based upon said primary characteristic determined by said means for coarse analysis;

(e) first means for fine analysis of said treated biological fluid associated with said first fluid path for determining a secondary characteristic of said treated biological fluid;

(f) first secondary valve means positioned downstream of said first means for fine analysis for selectively directing said treated biological fluid to third or fourth fluid paths based upon said secondary characteristic determined by said first means for fine analysis, said third fluid path supplying said treated biological fluid to a patient;

(g) second means for fine analysis of said treated biological fluid in fluid communication with said second fluid path for determining a secondary characteristic of said treated biological fluid; and (h) second secondary valve means positioned downstream of said second means for fine analysis for selectively directing said treated biological fluid to fifth or sixth fluid paths based upon said secondary characteristics determined by said second means for fine analysis, said second means for fine analysis of said treated biological fluid being a pH meter and a protein detector positioned serially for the monitoring of said fraction to be separated.

5. An apparatus for the separation of a fraction from a biological fluid to provide a treated biological fluid to be supplied to a patient, said apparatus utilizing an adsorption column having an adsorption medium thereon comprising:

(a) means for feeding said biological fluid into said adsorption column so as to adsorb said fraction into said column and produce a treated biological fluid therein;

(b) means for coarse analysis of said treated biological fluid for determining the degree of dilution of said treated biological fluid;

(c) means for supplying said treated biological fluid from said adsorption column to said means for coarse analysis;

(d) primary valve means positioned downstream of said means for coarse analysis for selectively directing said treated biological fluid to first or second fluid paths based upon said degree of dilution determined by said means for coarse analysis;

(e) first means for fine analysis of said treated biological fluid associated with said first fluid path for determining the pH of said treated biological fluid;

(f) a drain;

(g) first secondary valve means positioned downstream of said first means for fine analysis for selectively directing said treated biological fluid to third or fourth fluid paths based upon said pH determined by said first means for fine analysis, said third fluid path supplying said treated biological fluid to a patient and said fourth fluid path directing said treated biological fluid to said drain;

(h) second means for fine analysis of said treated biological fluid in fluid communication with said second fluid path for determining the protein content of said treated biological fluid;

(i) a collecting receiver; and (j) second secondary valve means positioned downstream of said second means for fine analysis for selectively directing said treated biological fluid to fifth or sixth fluid paths based upon said protein content determined by said second means for fine analysis, said fifth fluid path directing said treated biological fluid to said drain and said sixth fluid path directing said treated biological fluid to said collecting receiver.

6. The apparatus for the separation of a fraction from a biological fluid as defined in claim 5, wherein said means for supplying said treated biological fluid comprises a removable, disposable portion through which said treated biological fluid flows and arranged within said means for coarse analysis, said disposable portion having walls separating said treated biological fluid from said means for coarse analysis and through which said means for coarse analysis is operative for determining said degree of dilution of said treated biological fluid, whereby said disposable portion can be replaced while retaining said means for coarse analysis.

7. An apparatus for the separation of a fraction from a biological fluid to provide a treated biological fluid to be supplied to a patient, said apparatus utilizing an adsorption column having an adsorption medium thereon comprising:

(a) means for feeding said biological fluid into said adsorption column so as to adsorb said fraction into said column and produce a treated biological fluid therein;

(b) means for coarse analysis of said treated biological fluid for determining a primary characteristic of said treated biological fluid;

(c) means for supplying said treated biological fluid from said adsorption column to said means for coarse analysis, said means for supplying said treated biological fluid including a removable, disposable portion through which said treated biological fluid flows and arranged within said means for coarse analysis, said disposable portion having walls separating said treated biological fluid from said means for coarse analysis and through which said means for coarse analysis is operative for determining said primary characteristic of said treated biological fluid, whereby said disposable portion can be replaced while retaining said means for coarse analysis;

(d) primary valve means positioned downstream of said means for coarse analysis for selectively directing said treated biological fluid to first or second fluid paths based upon said primary characteristic determined by said means for coarse analysis;

(e) first means for fine analysis of said treated biological fluid associated with said first fluid path for determining a secondary characteristic of said treated biological fluid;

(f) first secondary valve means positioned downstream of said first means for fine analysis for selectively directing said treated biological fluid to third or fourth fluid paths based upon said secondary characteristic determined by said first means for fine analysis, said third fluid path supplying said treated biological fluid to a patient;

(g) second means for fine analysis of said treated biological fluid in fluid communication with said second fluid path for determining a secondary characteristic of said treated biological fluid;

(h) second secondary valve means positioned downstream of said second means for fine analysis for selectively directing said treated biological fluid to fifth or sixth fluid paths based upon said secondary characteristics determined by said second means for fine analysis;

(i) a second adsorption column positioned parallel to said first adsorption column;

(j) second means for feeding said biological fluid into said second adsorption column so as to adsorb said fraction into said column and produce a treated biological fluid therein;

(k) second means for coarse analysis of said treated biological fluid for determining said primary characteristic of said treated biological fluid;

(l) second means for supplying said treated biological fluid from said second adsorption column to said second means for coarse analysis, said second means for supplying said treated biological fluid including a removable, disposable portion through which said treated biological fluid flows and arranged within said second means for coarse analysis, said disposable portion having walls separating said treated biological fluid from said second means for coarse analysis and through which said second means for coarse analysis is operative for determining said primary characteristic of said treated biological fluid, whereby said disposable portion can be replaced while retaining said second means for coarse analysis; and (m) second primary valve means positioned downstream of said second means for coarse analysis for selectively directing said treated biological fluid to said first or second fluid paths based upon said primary characteristic determined by said second means for coarse analysis, each of said means for coarse analysis comprising a detector for monitoring a degree of dilution of said treated biological fluid.

* * * * *